US009883089B2

(12) United States Patent
Urakawa et al.

(10) Patent No.: US 9,883,089 B2
(45) Date of Patent: Jan. 30, 2018

(54) IMAGING UNIT

(71) Applicant: OLYMPUS CORPORATION, Tokyo (JP)

(72) Inventors: Tsutomu Urakawa, Hachioji (JP); Hideaki Kinouchi, Musashino (JP); Takamasa Mikami, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/851,157

(22) Filed: Sep. 11, 2015

(65) Prior Publication Data

US 2016/0006915 A1 Jan. 7, 2016

Related U.S. Application Data

(63) Continuation of application No. PCT/JP2014/077526, filed on Oct. 16, 2014.

(30) Foreign Application Priority Data

Feb. 21, 2014 (JP) .................................. 2014-031767

(51) Int. Cl.
*A61B 1/05* (2006.01)
*H04N 5/225* (2006.01)
(Continued)

(52) U.S. Cl.
CPC ............. *H04N 5/2256* (2013.01); *A61B 1/05* (2013.01); *A61B 1/051* (2013.01);
(Continued)

(58) Field of Classification Search
CPC ...... A61B 1/05; A61B 1/051; G02B 23/2484; H04N 2005/2255; H04N 5/2256; H04N 5/2354
(Continued)

(56) References Cited

U.S. PATENT DOCUMENTS 4,473,841 A * 9/1984 Murakoshi ......... A61B 1/00013
128/901
5,258,834 A * 11/1993 Tsuji ....................... H04N 7/18
348/270
(Continued)

FOREIGN PATENT DOCUMENTS

CN 101808568 A 8/2010
CN 102240203 A 11/2011
(Continued)

OTHER PUBLICATIONS

International Search Report dated Jan. 20, 2015 issued in PCT/JP2014/077526.
(Continued)

*Primary Examiner* — Deirdre Beasley
(74) *Attorney, Agent, or Firm* — Scully, Scott, Murphy & Presser, P.C.

(57) ABSTRACT

An imaging unit provided at a tip portion of an endoscope includes: an imaging element configured to receive light and perform photoelectric conversion on the light to generate an electrical signal; an oscillator configured to generate a clock signal for driving the imaging element; a photoelectric element configured to convert the electrical signal generated by the imaging element into an optical signal and to output the optical signal to outside; a regulator configured to convert electric power input from the outside into electric power depending on each of the imaging element, the oscillator, and the photoelectric element, and to supply the converted electric power thereto. The imaging element is spaced farther than the oscillator and the photoelectric element from the regulator.

2 Claims, 2 Drawing Sheets

(51) Int. Cl.
*H04N 5/235* (2006.01)
*G02B 23/24* (2006.01)

(52) U.S. Cl.
CPC ....... *G02B 23/2484* (2013.01); *H04N 5/2354* (2013.01); *H04N 5/2254* (2013.01); *H04N 2005/2255* (2013.01)

(58) Field of Classification Search
USPC .......................................... 348/68
See application file for complete search history.

(56) References Cited

U.S. PATENT DOCUMENTS

| | | | |
|---|---|---|---|
| 6,099,465 A | 8/2000 | Inoue | |
| 2004/0073086 A1* | 4/2004 | Abe | H04N 5/23203 600/109 |
| 2005/0197536 A1* | 9/2005 | Banik | A61B 1/00059 600/179 |
| 2005/0203338 A1* | 9/2005 | Couvillon, Jr. | A61B 1/00013 600/109 |
| 2007/0177010 A1* | 8/2007 | Murata | G02B 23/2492 348/74 |
| 2007/0230075 A1* | 10/2007 | Murata | G02B 23/2492 361/58 |
| 2007/0232860 A1* | 10/2007 | Kubo | A61B 1/00006 600/160 |
| 2009/0207240 A1* | 8/2009 | Kashima | A61B 1/05 348/65 |
| 2011/0292194 A1* | 12/2011 | Kato | A61B 1/00009 348/65 |
| 2013/0030248 A1* | 1/2013 | Matsumaru | A61B 1/00027 600/110 |
| 2013/0169775 A1* | 7/2013 | Ono | A61B 1/00009 348/68 |

FOREIGN PATENT DOCUMENTS

| | | |
|---|---|---|
| JP | 2002-291693 A | 10/2002 |
| JP | 2003-052628 A | 2/2003 |
| JP | 2005-074035 A | 3/2005 |
| JP | 2010-051503 A | 3/2010 |
| JP | 2011-206333 A | 10/2011 |
| JP | 2011-224349 A | 11/2011 |
| JP | 2013-175861 A | 9/2013 |

OTHER PUBLICATIONS

Japanese Decision of a Patent Grant dated Jun. 3, 2015 issued in JP 2015-511837.

* cited by examiner

IMAGING UNIT

CROSS-REFERENCE TO RELATED APPLICATIONS

This application is a continuation of PCT international application Ser. No. PCT/JP2014/077526 filed on Oct. 16, 2014 which designates the United States, incorporated herein by reference, and which claims the benefit of priority from Japanese Patent Application No. 2014-031767, filed on Feb. 21, 2014, incorporated herein by reference.

BACKGROUND

1. Technical Field

The disclosure relates to an imaging unit provided at a tip of an insertion unit of an endoscope that is to be inserted into a subject for imaging inside of the subject.

2. Related Art

Conventionally, in the medical field and the industrial field, endoscopes have been used widely in a variety of examinations. Among them, a medical endoscope obtains an in-vivo image of inside of a body cavity of the subject by inserting a flexible insertion unit having an elongated shape and provided with an imaging element at a tip thereof into the body cavity of the subject such as a patient.

There has been known a technique in which an imaging unit is provided at a tip portion of such endoscope. The imaging unit includes a circuit board on which an imaging element, electronic components such as a capacitor and an IC chip constituting a driving circuit for driving the imaging element, and a regulator for supplying electric power to each of the electronic components are mounted (see Japanese Patent Application Laid-open No. 2003-52628).

SUMMARY

In some embodiments, an imaging unit provided at a tip portion of an endoscope includes: an imaging element configured to receive light and perform photoelectric conversion on the light to generate an electrical signal; an oscillator configured to generate a clock signal for driving the imaging element; a photoelectric element configured to convert the electrical signal generated by the imaging element into an optical signal and to output the optical signal to outside; a regulator configured to convert electric power input from the outside into electric power depending on each of the imaging element, the oscillator, and the photoelectric element, and to supply the converted electric power thereto. The imaging element is spaced farther than the oscillator and the photoelectric element from the regulator.

The above and other features, advantages and technical and industrial significance of this invention will be better understood by reading the following detailed description of presently preferred embodiments of the invention, when considered in connection with the accompanying drawings.

DETAILED DESCRIPTION

Modes for carrying out the present invention (hereinafter referred to as "embodiment(s)") will be described below. In this embodiment, as an example of an imaging system, reference will be made to a medical endoscope system for imaging and displaying an image inside of a body cavity of a subject such as a patient. Note that the present invention is not to be limited by the embodiments below. The same reference signs are used to designate the same elements throughout the drawings.

Figure 1:
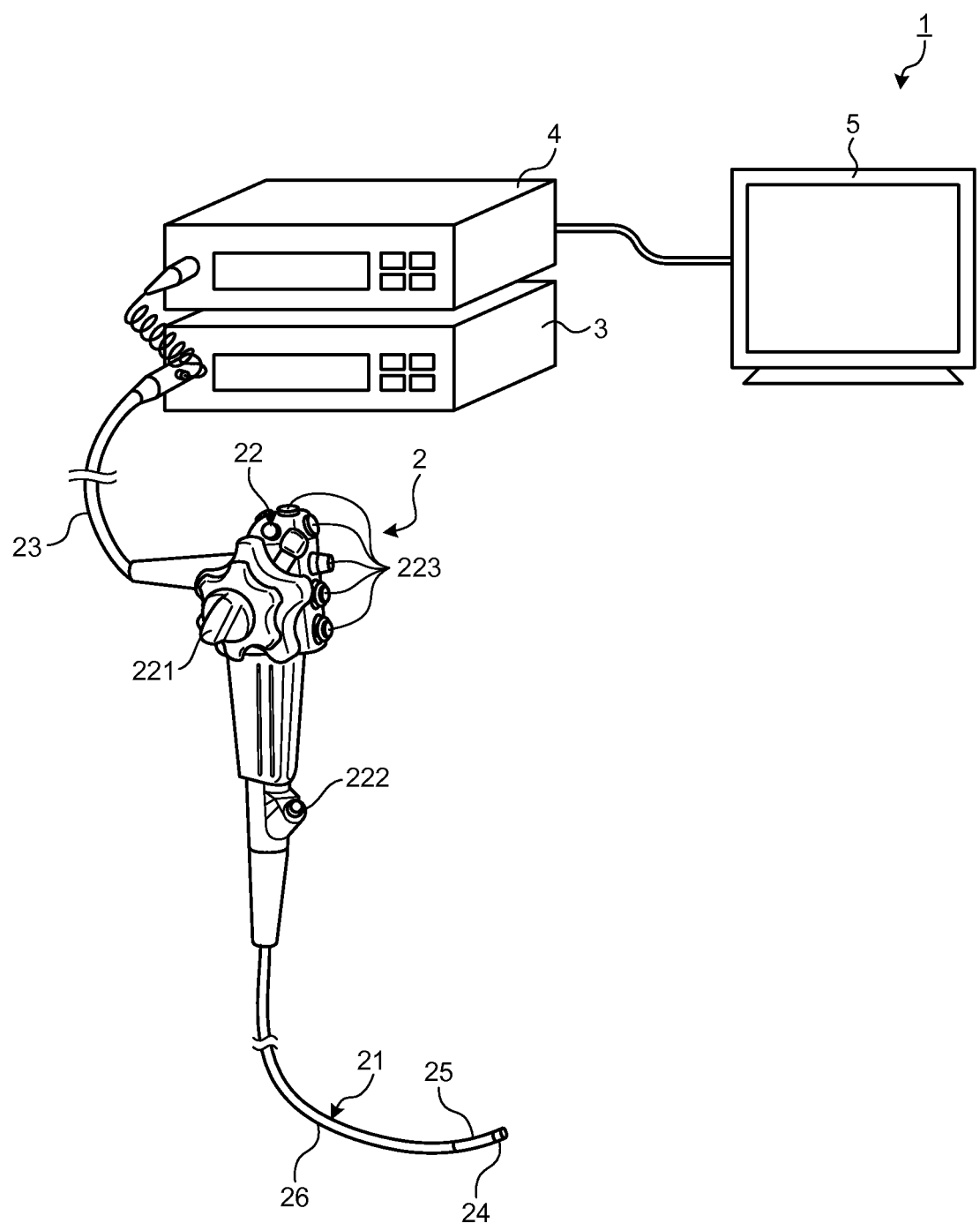
FIG. 1 is a schematic view illustrating a configuration of an endoscope system according to one embodiment of the present invention.

FIG. 1 is a schematic view illustrating a configuration of an endoscope system according to one embodiment of the present invention. An endoscope system 1 illustrated in FIG. 1 includes an endoscope 2 that images an in-vivo image of the subject by inserting a tip portion thereof into the body cavity of the subject, a light source device 3 that generates illumination light to be emitted from a tip of the endoscope 2, a processing device 4 (control device) that performs predetermined image processing on the in-vivo image imaged by the endoscope 2 as well as totally controls operation of the endoscope system 1 as a whole, and a display device 5 that displays the in-vivo image on which the image processing has been performed by the processing device 4.

First, a configuration of the endoscope 2 will be described. The endoscope 2 includes an flexible insertion unit 21 having a thin elongated shape, an operating unit 22 connected to a proximal end side of the insertion unit 21 and that receives input of various operation signals, and a universal code 23 extending from the operating unit 22 to a direction different from a direction in which the insertion unit 21 extends and incorporating various cables that connect to the light source device 3 and the processing device 4.

The insertion unit 21 includes a tip portion 24 incorporating an imaging element (imaging device) in which a picture element, which generates a signal by receiving light and performing photoelectric conversion, is two-dimensionally arranged, a bendable bent portion 25 including a plurality of bent pieces, and a long flexible pipe portion 26 connected with a proximal end side of the bent portion 25.

The operating unit 22 includes a bent knob 221 that bends the bent portion 25 in a vertical direction and a horizontal direction, a treatment tool insertion unit 222 through which a treatment tool such as a biological forceps, an electric knife, and an inspection probe are configured to be inserted into the body cavity of the subject, and a plurality of switches 223 that is an operating input unit for inputting an operating instruction signal of a peripheral device such as an air feed means, a water feed means, and an image display control in addition to the processing device 4 and the light source device 3. The treatment tool, which is inserted through the treatment tool insertion unit 222, appears from an opening portion (not illustrated) after going through a treatment tool channel (not illustrated) of the tip portion 24.

The universal code 23 has at least a light guide (not illustrated) for transmitting the illumination light from the light source device 3, and a plurality of signal lines for transmitting a clock signal, a synchronizing signal, and the like for driving the imaging element provided at the tip portion 24 from the processing device 4.

Figure 2:
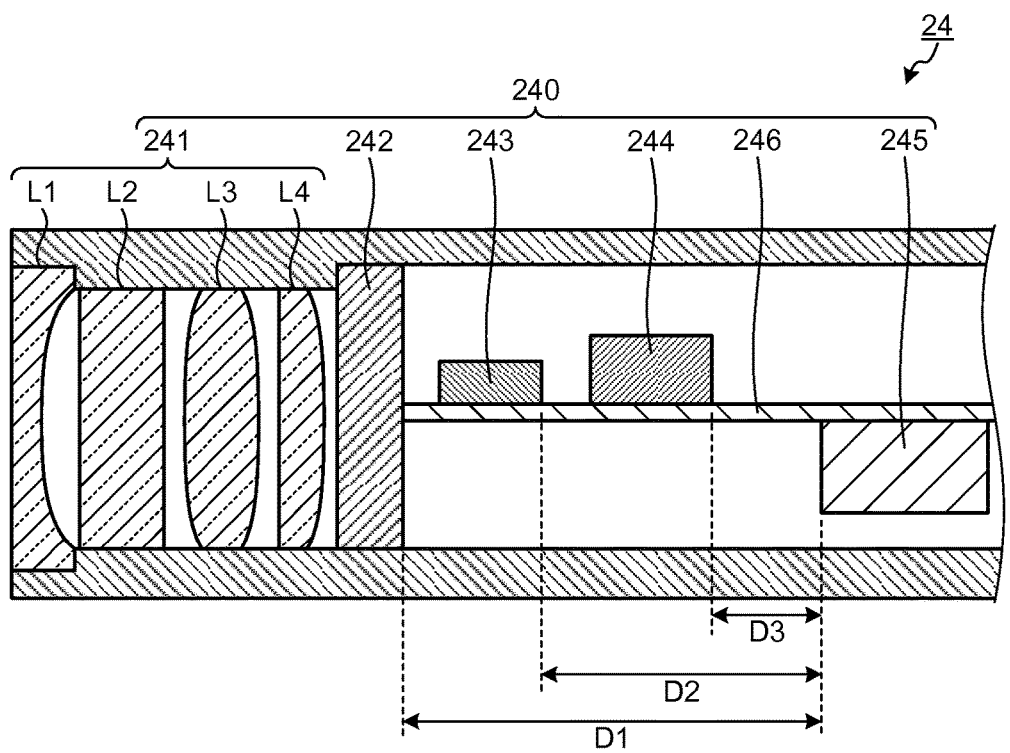
FIG. 2 is a partial sectional view of a tip portion of an endoscope in the endoscope system according to one embodiment of the present invention.

Next, a configuration of the tip portion 24 of the endoscope 2 will be described in detail. FIG. 2 is a partial sectional view of the tip portion 24 of the endoscope 2.

As illustrated in FIG. 2, the tip portion 24 has an imaging unit 240 therein. The imaging unit 240 includes an optical system 241 that forms an image of the object, an imaging element 242 that generates an image signal (image data) of the object by receiving the image of the object that has been formed by the optical system 241 and by performing photoelectric conversion thereon, an oscillator 243 that emits a signal for driving the imaging element 242, a photoelectric element 244 that outputs the image signal that has been generated by the imaging element 242 to the processing device 4, a regulator 245 that supplies electric power to each of components of the imaging unit 240, and a flexible printed circuit board 246 (hereinafter, referred to as "FPC board 246") on which the oscillator 243, the photoelectric element 244, and the regulator 245 are disposed.

The optical system 241 includes a plurality of objective lenses L1 to L4 and forms the image of the object that is irradiated with the illumination light from the light source device 3. Note that the optical system 241 may include a crossed prism, a condenser lens, a collimator lens, and the like.

The imaging element 242 is arranged to an image formation position in which the image of the object is formed by the optical system 241, and the imaging element 242 generates an image signal of the object by receiving the image of the object, which is formed by the optical system 241, and by performing photoelectric conversion thereon. The imaging element 242 outputs this image signal to the photoelectric element 244. The imaging element 242 includes a solid imaging element such as a charge coupled device (CCD) or a complementary metal oxide semiconductor (CMOS). The imaging element 242 generates the image signal based on the clock signal that is output from the oscillator 243, and outputs the generated image signal to the photoelectric element 244. Inside the tip portion 24, the imaging element 242 is positioned farther than the oscillator 243 and the photoelectric element 244 from the regulator 245.

The oscillator 243 generates the clock signal for driving the imaging element 242. The oscillator 243 is disposed on an upper surface of the FPC board 246. Inside the tip portion 24, the oscillator 243 is positioned farther than the photoelectric element 244 from the regulator 245.

The photoelectric element 244 converts the image signal (electrical signal) that has been output from the imaging element 242 into an optical signal, and the optical signal that has been converted is output to the processing device 4. A cable connecting the photoelectric element 244 with the processing device 4 includes an optical fiber and the like.

The regulator 245 converts electric power that is supplied from the processing device 4 through the universal code 23 into electric power useable by each of the imaging element 242, the oscillator 243, and the photoelectric element 244 and supplies this converted electric power to each of the components. The regulator 245 is disposed on a back surface of the FPC board 246.

In the imaging unit 240 having such configuration, considering an influence of heat, the optical system 241, the imaging element 242, the oscillator 243, the photoelectric element 244, and the regulator 245 are arranged in this order from an end of the tip portion 24. Specifically, in the imaging unit 240, the imaging element 242, the oscillator 243, and the photoelectric element 244 are spaced from the regulator 245 in this order. For example, in the imaging unit 240, when a distance between the imaging element 242 and the regulator 245 is denoted by D1, a distance between the oscillator 243 and the regulator 245 is denoted by D2, and a distance between the photoelectric element 244 and the regulator 245 is denoted by D3, D1>D2>D3 is satisfied.

According to one embodiment of the present invention described above, the optical system 241, the imaging element 242, the oscillator 243, the photoelectric element 244, and the regulator 245 are arranged in this order from the end of the tip portion 24. The regulator 245 having the largest heating value is positioned inside the tip portion 24 farthest from the imaging element 242 which is the most affected by heat. Thus even when temperature of the tip portion 24 or temperature of the regulator 245 is increased, it is possible to reduce noise that occurs in the image signal generated by the imaging element 242.

According to some embodiments, it is possible to reduce noise that occurs in the image signal generated by the imaging element.

In this way, the present invention may include various embodiments not described herein, and it is possible to add various design changes and the like within a scope of technical ideas specified by claims.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging unit provided at a tip portion of an endoscope, the imaging unit comprising:
   an optical system configured to form an optical image;
   an imaging element configured to perform photoelectric conversion on the optical image to generate an electrical signal;
   a housing for holding the optical system and the imaging element;
   a board disposed inside the housing and extending along a longitudinal direction of the housing;
   an oscillator disposed on the board and configured to generate a clock signal for driving the imaging element;
   a photoelectric element disposed on the board and configured to convert the electrical signal generated by the imaging element into an optical signal and to output the optical signal to outside;
   a regulator disposed on the board and configured to convert electric power input from the outside into electric power depending on each of the imaging element, the oscillator, and the photoelectric element, and to supply the converted electric power thereto, wherein
   the regulator having a larger heating value than respective heating values of the imaging element, the oscillator, and the photoelectric element, the imaging element is spaced farther than the oscillator and the photoelectric element from the regulator,
   the oscillator, the photoelectric element, and the regulator are disposed on the board along the longitudinal direction of the housing,
   the oscillator and the photoelectric element disposed on the board are positioned between the imaging element and the regulator; and
   wherein the oscillator is spaced farther than the photoelectric element from the regulator on the board.

2. The imaging unit according to claim 1, wherein the oscillator and the photoelectric element are disposed on a first surface of the board, and the regulator is disposed on a second surface of the board opposite to the first surface.

* * * * *